United States Patent [19]
Müller et al.

[11] Patent Number: 5,963,575
[45] Date of Patent: Oct. 5, 1999

[54] Q-SWITCHED LASER SYSTEM, IN PARTICULAR FOR LASER LITHOTRIPSY

[75] Inventors: Gerhard Müller, Berlin, Germany; Pavel Pashinin, Moskau/Moscow, Russian Federation

[73] Assignee: Clyxon Laser Für Mediziner GmbH, Berlin, Germany

[21] Appl. No.: 08/968,765

[22] Filed: Sep. 22, 1997

Related U.S. Application Data

[63] Continuation of application No. 08/525,777, filed as application No. PCT/DE94/00362, Mar. 28, 1994, abandoned.

[30] Foreign Application Priority Data

Mar. 27, 1993 [DE] Germany .............................. 43 10 023
Oct. 29, 1993 [DE] Germany .............................. 43 36 947

[51] Int. Cl.[6] .................................................. H01S 3/08
[52] U.S. Cl. .............................. 372/92; 372/10; 372/6; 372/98; 372/64; 372/69; 372/25
[58] Field of Search ................................ 372/10, 22, 35, 372/98, 99, 92, 100, 25, 6, 64, 69

[56] References Cited

U.S. PATENT DOCUMENTS

| | | | |
|---|---|---|---|
| 3,633,126 | 1/1972 | Martin et al. | 372/35 |
| 4,525,842 | 7/1985 | Myers . | |
| 4,723,256 | 2/1988 | Hoag | 372/92 |
| 4,740,986 | 4/1988 | Reeder | 372/100 |
| 4,847,850 | 7/1989 | Kafka et al. | 372/10 |

(List continued on next page.)

FOREIGN PATENT DOCUMENTS

| | | |
|---|---|---|
| 380634 | 11/1985 | Austria . |
| 2644014 | 4/1977 | Germany . |
| 3690223 | 11/1986 | Germany . |
| 3813482 | 11/1989 | Germany . |
| 3933613 | 4/1991 | Germany . |
| 4029530 | 3/1992 | Germany . |
| 4130802 | 4/1992 | Germany . |
| 63291488 | 3/1989 | Japan . |

(List continued on next page.)

OTHER PUBLICATIONS

Nakazawa et al.: "Lasing Characteristics of a $Nd^{3+}$: YAG Laser with a long optical–fiber resonator". In: Journal of the optical Society of America, vol. 73, No. 6 Jun. 1983, New York, US, pp. 838–842.

Isaev et al.: "Mode self–locking in solid–state lasers with long resonators". In: Journal of the optical Society of Amrica, vol. 68, No. 11, Nov. 1978, New York, US, pp. 1621–1622.

Engelhardt et al. "1$\mu$s Alexandrite–Laser for Laser Induced Shockwave Lithotripsy". In: Laser und Opto–elektronik 21, 6, 1989, pp. 56–61.

Schmid: "Pulse Stretching in a Q–Switched Nd: YAG Laser". IEEE Journal of Quantum–Electronics, vol. QE–16, No. 7, Jul. 1980, pp. 790–794.

Steiger: "A Q–switched Alexandrite Laser for Laser Induced Shock Wave Lithotripsy (LISL)". In: Laser und Optoelektronik 20, 4, 1988, pp. 40–43.

Shen et al.: "Research note. Large energy 1341.4 nm Nd: $YALO_3$ pulse laser". In: Optics & Laser Technology, vol. 23, No. 6,f 1991, pp. 366–367.

Ryan et al.: "Optical absorption and stimulated emission of neodymium inyttrium lithium flouride". In: Optical Society of America, vol. 9, No. 10, Oct. 1992, pp. 1883–1887.

Walter Koechner "Solid–State Laser Engineering" (1992), p. 438.

*Primary Examiner*—Leon Scott, Jr.
*Attorney, Agent, or Firm*—Venable; George H. Spencer; Allen Wood

[57] ABSTRACT

A Q-switched laser system, in particular for laser lithotripsy, has a laser-active medium (2.1) in a resonator, an optical pumping arrangement (2.3) and a passive Q-switch (3.2). A resonator extension (1.2) having an optical waveguide is associated to the laser-active medium (2.1) in order to increase the laser pulse length.

30 Claims, 2 Drawing Sheets

U.S. PATENT DOCUMENTS

| | | | |
|---|---|---|---|
| 4,890,289 | 12/1989 | Basu et al. | 372/6 |
| 4,912,713 | 3/1990 | Langhans | 372/100 |
| 4,930,901 | 6/1990 | Johnson et al. | 372/10 |
| 5,008,887 | 4/1991 | Kafka et al. | 372/6 |
| 5,140,600 | 8/1992 | Rebhan | 372/25 |
| 5,151,909 | 9/1992 | Davenport et al. | 372/10 |
| 5,363,387 | 11/1994 | Sinofsky | 372/25 |
| 5,394,413 | 2/1995 | Zayhowski | 372/10 |
| 5,422,899 | 6/1995 | Freiberg et al. | 372/35 |
| 5,434,875 | 7/1995 | Reiger et al. | 372/25 |
| 5,491,707 | 2/1996 | Rieger et al. | 372/10 |
| 5,546,416 | 8/1996 | Basu | 372/92 |

FOREIGN PATENT DOCUMENTS

| | | |
|---|---|---|
| 3293788 | 4/1992 | Japan . |
| 1704772 | 1/1992 | U.S.S.R. . |
| 90/04358 | 5/1990 | WIPO . |
| 90/12544 | 11/1990 | WIPO . |
| 91/05332 | 4/1991 | WIPO . |
| 91/05380 | 4/1991 | WIPO . |
| 91/17593 | 11/1991 | WIPO . |

Q-SWITCHED LASER SYSTEM, IN PARTICULAR FOR LASER LITHOTRIPSY

This application is a Continuation of application Ser. No. 08/525,777, filed Dec. 21, 1995, now abandoned, which is filed as PCT/DE94/00362 filed on Mar. 28, 1994.

BACKGROUND OF THE INVENTION

The invention relates to a Q-switched laser system of the type which includes a laser-active medium in a resonator construction, an arrangement for optical pumping, and a passive Q-switch.

Solid-body laser systems for laser lithotripsy are known from the publications WO 90/12544, WO 90/04358, WO 91/05332 and AT-B-380634. In these systems, which operate with short, single pulses, the fiber which transmits the energy to the location of application is destroyed very quickly in practical use because of the short pulse lengths used in the systems. Moreover, the technical structures of these laser systems are very cost- and maintenance-intensive.

In addition, experimental investigations have revealed that it is favorable to operate with a so-called double pulse in laser lithotripsy, which involves the transmission in rapid succession of two pulses to the location of application, with the one pulse being shifted toward the actual energy-carrying pulse toward the short-wave range ("blue") typically representing the harmonic of the carrier wave length. This combination permits premature ignition of the optical breakdown (plasma) at the rock surface to be broken up, and thus allows for a greater effectiveness in rock breaking. However, the disadvantage associated herewith is rapid fiber burnup in practical use.

SUMMARY OF THE INVENTION

It is therefore the object of the invention to disclose a Q-switched laser system of the generic type mentioned at the outset which is particularly suited for laser lithotripsy, generates laser pulses that do not lead to premature wear of the transmission fibers, operates efficiently and can be produced cost-effectively.

This object is accomplished by a laser system in which a resonator extension is provided for increasing the laser pulse length, the resonator extension including an optical waveguide.

With the known state of the art as a point of departure, it has been seen that, surprisingly, the efficiency of rock breaking in laser lithotripsy not only depends on the earliest possible ignition of a plasma and the resulting shock wave and the production of cavitation bubbles, but is primarily determined by the fulfillment of an inclusion condition for the plasma with a subsequent compressional shock.

Surprisingly, the theoretical and experimental investigations by the inventors were able to corroborate that optimal inclusion conditions are given when one takes into consideration the delay time of the acoustical shock waves with the retention of certain relationships between the pulse duration and the geometry of the end surface of the fiber that transmits the energy to the location of application. The rule of thumb was found to be that the pulse duration for the optimal inclusion condition corresponds in nanoseconds to 1.5 times the diameter of the energy-applying fibers in micrometers. This means that, for example, in a Q/Q fiber having a 360 $\mu$m core and—depending on the manufacturer—having a diameter at the optical cladding of approximately 400 to 420 $\mu$m, the optimum pulse duration for the lithotripsy is approximately 600 to 650 ns.

The invention therefore incorporates the concept of configuring the generic laser system such that it delivers corresponding pulses whose length—depending on the application fiber that is used—is particularly between 200 ns and 1 $\mu$s, possibly up to a few $\mu$s. However, conventional laser-active media and media which are preferred for cost reasons, such as neodymium-doped laser crystals, especially Nd:YAG and Nd:YAlO$_3$, only have pulse durations between 7 and 15 ns in normal Q-switched operation.

According to the invention, this limitation is overcome by an optical extension of the resonator by means of a long optical waveguide. (A resonator extension using an optical waveguide approximately 18 m in length is typically required for a pulse duration of approximately 650 ns.)

The effect achieved with this measure is that, not only can the pulse duration of the laser system be altered cost-effectively in broad ranges as a function of the length of the waveguide—particularly between 200 ns and a few $\mu$s without the emitted pulse peak output being significantly changed (variations <10% were determined), but that simultaneously achieved are a smoothing of the disadvantageous, statistical intensity oscillations (so-called "spikes") which occur during a laser pulse and lead to increased fiber wear, and homogenization of the spatial intensity profile with suppression of excessive intensity elevations in the beam cross-section (so-called "hot spots"). The consequential creation of spatially and temporally smoothed pulse profiles is of considerable advantage for the transmission of the pulses by means of coupled-on, external light waveguides. In particular, it extends their service life significantly.

The invention also includes the concept of stimulating the laser-active medium with a pumping energy which is higher than the pump energy necessary for generating single pulses; with this higher energy, pulse cascades ("bursts") can be produced which—corresponding to the above-described operational conditions of laser pulse radiation in laser lithotripsy—have advantages in terms of effectiveness vis-a-vis single pulses.

DESCRIPTION OF THE PREFERRED EMBODIMENTS

Figure 1A:
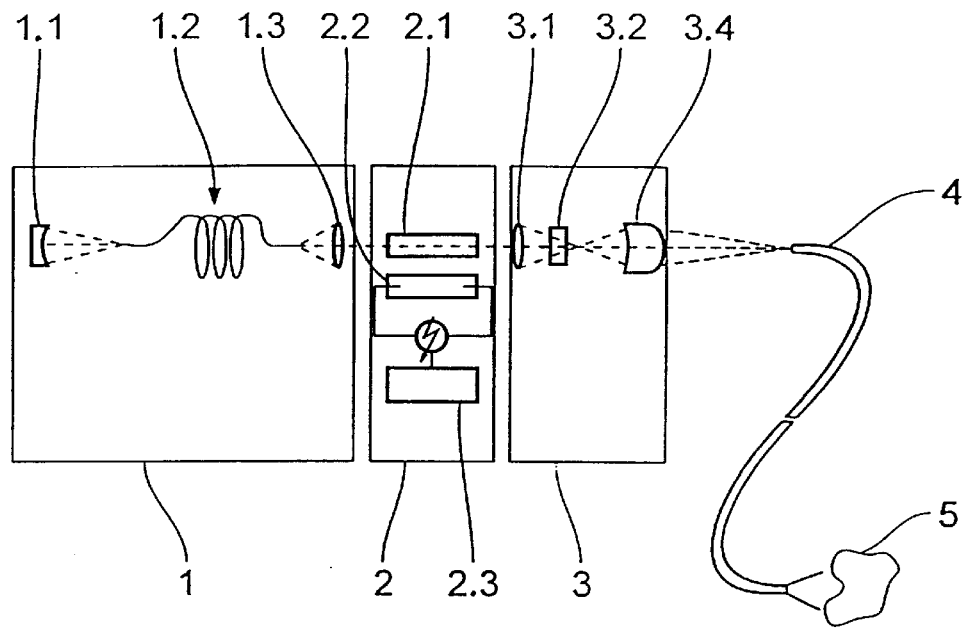
FIG. 1a is a schematic representation of a laser system according to an embodiment of the invention.

FIG. 1a schematically shows a preferred optical arrangement of a long-pulse, solid-body lithotripsy laser as an embodiment of the invention. In this instance, an assembly 1 comprises a focussing lens 1.3, a fiber-optic resonator extension 1.2 and an arched resonator end mirror 1.1, whose arch and spacing from the exit of the fiber of the resonator extension (1.2) are dimensioned such that, taking into consideration the numerical aperture of the fiber, the radius of curvature corresponds approximately to half the distance between the fiber end surface and the mirror surface.

An assembly 2 includes a conventional laser cavity. Here 2.1 indicates a laser crystal, preferably Nd:YAG or Nd:YAlo3, 2.2 indicates a flash lamp for optical pumping, and 2.3 a unit for energy supply and system control.

An assembly 3 includes a partially-transparent resonator end mirror 3.4, a non-linear crystal 3.3 for frequency doubling, typically a KTP crystal, and a passive Q-switch 3.2, typically Cr 4+:YAG or LiF(F2-), and a relay optics 3.1 for collimating the radiation.

In an advancement of the concept of the invention, a further increase in the efficiency in producing the first harmonic can be achieved by means of the insertion of a polarization-optical assembly, comprising a Brewster angle polarizer and a retroreflector at essentially a right angle thereto, between either the components 3.2 and 3.3 of the assembly 1 or components 3.2 and 3.3 of the assembly 3.

Assuming the use of a neodymium-doped YAG laser crystal having a 5 mm diameter and 5 cm length, and a pumping energy at the flash lamp of approximately 30 J, the following, typical initial values can be achieved for the preferred embodiment: pulse duration, adjustable between 200 ns and 1 µs, depending on the length of the fiber extension in the resonator, with an approximate 20 m fiber length, mJ at 1064 nm base emission and approximately 15 Mj at 532 nm (second harmonic), assuming a base absorption of the passive Q-switch of approximately 25%. With variations in pulse length of 200 ns to 1 µs, the input energy only changes by about 10%. In the use of polarized laser radiation, the initial energy of the second harmonic increases to approximately 22 to 25 mJ either by means of the insertion of the above-mentioned additional elements of the use of a double-refracting laser material, for example Nd:YAlO$_3$. In this case, the core diameter of the resonator extension is only 280 µm, so that, taking into consideration the divergence stipulated by the numerical aperture, the transmission of the total emitted energy by means of a Q/Q fiber 4 having a 360 µm core diameter is possible for use in lithotripsy on a rock 5.

According to the invention, a further increase in shattering efficiency in lithotripsy is achieved by means of stimulation of the laser crystal with a pumping energy which is higher than the pumping energy necessary to generate single pulses. A consequence of the increase by 30%, i.e., to approximately 40 J, is the emission of a cascade of single pulses whose temporal spacing is approximately 50 µs with a base absorption of the Q-switch of 25%, and whose temporal spacing can be approximately halved when the base absorption is increased by a factor of 2. This pulse cascade (also called burst) leads to a significant increase in the shattering efficiency on the rock 5 in lithotripsy, because the sequential pulses can be used directly to generate sequential compressional shocks by means of the optimized inclusion conditions.

Another possible embodiment of the above-described arrangement is as a solid-body laser having an erbium-doped laser crystal which emits wavelengths between 1.54 and 2.94 µm, depending on the host crystal or matrix. In this instance, the following laser media are particularly suited for use: erbium:YAG, erbium:YSSG and erbium:YAG co-doped with chromium and thulium, so-called CTE lasers. A zirconium fluoride fiber or an aluminum fluoride fiber is preferred as the waveguide.

In a modification of this embodiment, erbium glass lasers based on chalkogenide glasses (e.g. germanium, arsenic or sulfur glasses) are also used; fibers made of the same chalkogenide glass can be used as waveguides.

Optical crystals such as lithium niobate or lithium iodate are used as passive Q-switches. However, other known Q-switches besides these can also be used.

The use of lenses for focussing the beam inside the resonator can be omitted when the optical waveguide is provided at both ends with a taper-coupler (a coupling-in layer having an approximately wedge- or trumpet-shaped cross-section).

Figure 1B:
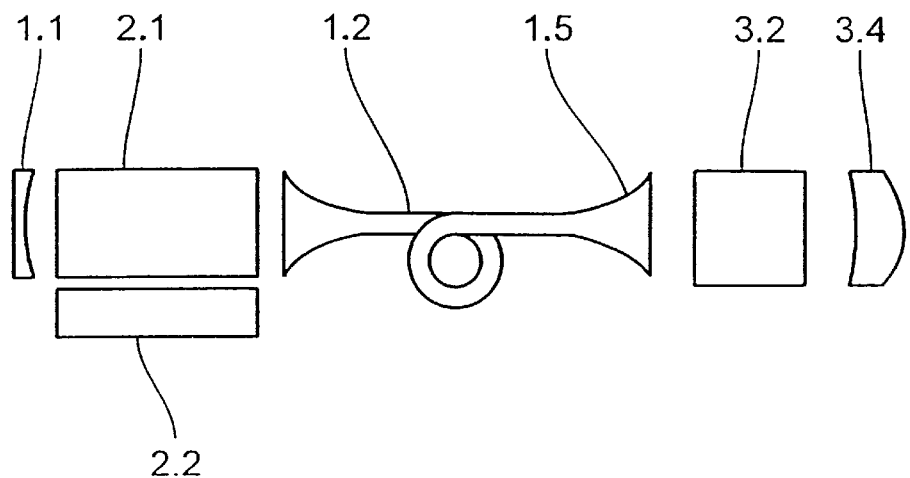
FIG. 1b is a schematic representation of the primary optical components of a laser system according to an embodiment of the invention which is modified with respect to FIG. 1a, FIG. 2a is the schematic representation of the path of the beam in a multi-pass waveguide as a component of a further embodiment of the invention.

FIG. 1b shows such a configuration having two tapers 1.5, which are spliced to the fiber-optical waveguide 1.2 as end pieces; this configuration is further modified with respect to the arrangement according to FIG. 1a, differing in the sequence of laser crystal 2.1 and waveguide 1.2 between mirror 1.1 and Q-switch 3.2 and the partially-transparent mirror 3.4, and in the configuration of the laser crystal as an erbium-doped crystal.

In a similar manner, holmium-doped, solid-body lasers and solid-body lasers having frequency multiplication in the blue and ultraviolet spectral range, and pulsed gas lasers, for example excimer lasers and nitrogen lasers, can also be implemented.

It is also possible to provide only one of the ends of the waveguide with a taper-coupler.

Figure 2A:
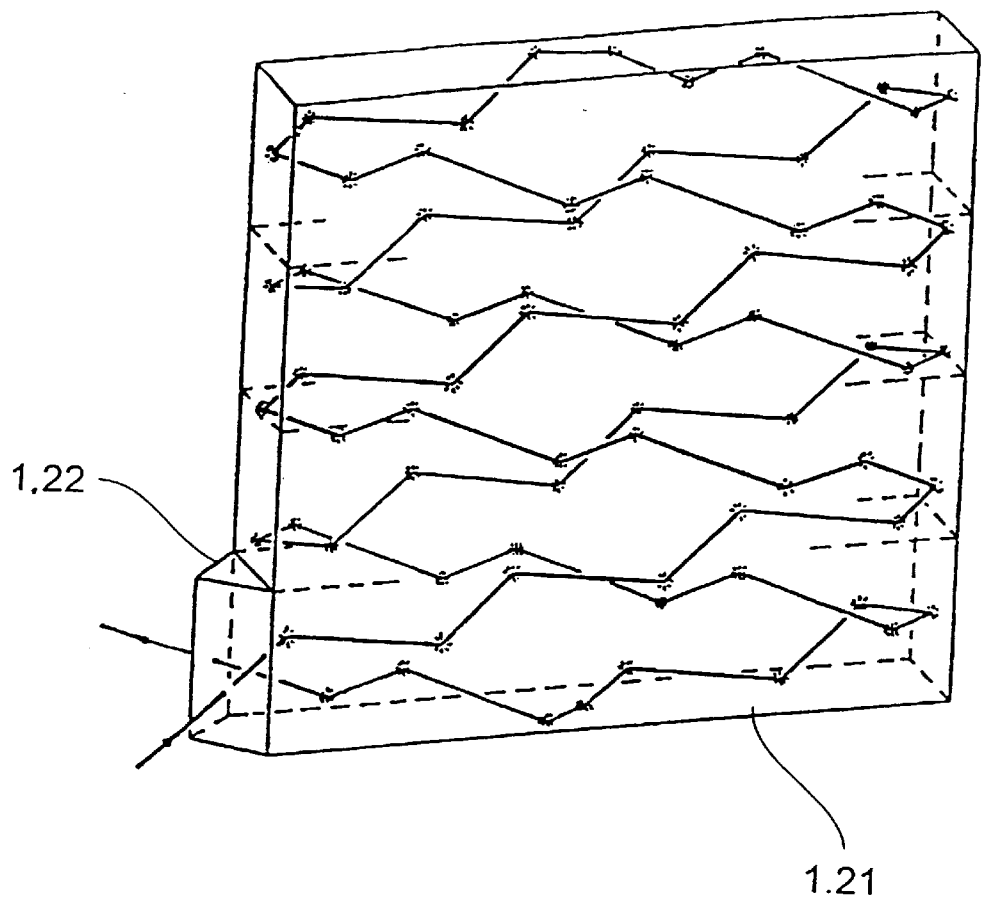
FIG. 2b is a schematic representation of the embodiment which includes the multi-pass waveguide.

In another embodiment of the concept of the invention, a planar optical waveguide can also be used in place of the optical fiber as a multi-pass reflection plate. An embodiment of such a planar multi-pass waveguide 1.21 is illustrated in FIG. 2a. As can be seen in FIG. 2a, this waveguide essentially has the shape of a flat cuboid or a plate which is provided with a coupling-in/-out segment 1.22, and whose large optical path length is effected by multiple beam passage with reflection at the walls of the cuboid.

Figure 2B:
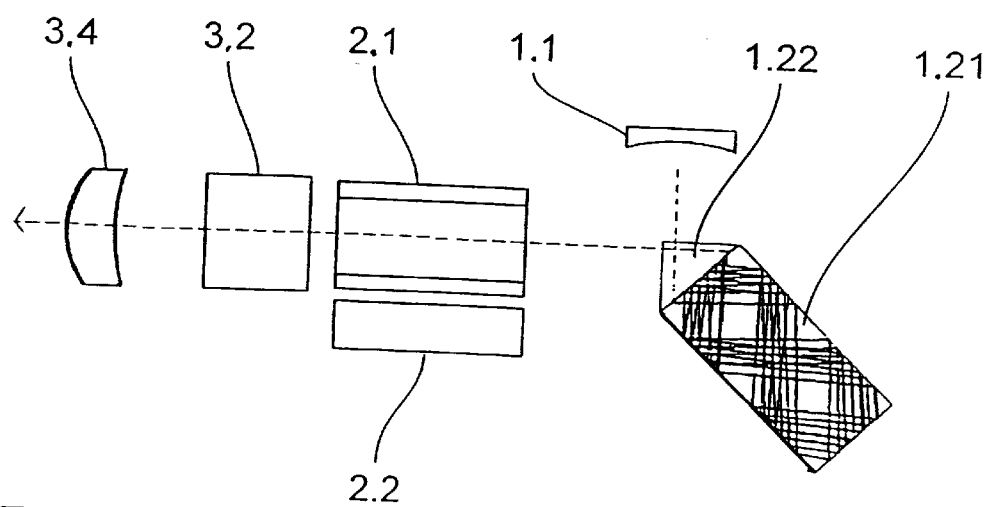

FIG. 2b shows an embodiment of the optical part of the laser system that extensively corresponds to the arrangement illustrated in FIG. 1b and uses a multi-pass waveguide 1.21 of the type shown in FIG. 2a in place of the wound fiber waveguide 1.2 shown in FIG. 1b. All other elements correspond to those in FIG. 1b, and are thus not explained again.

Examples of the material used for the planar optical waveguide—depending on the parameters of the generated laser beam—are chalkogenide glasses of suitable composition (e.g. germanium arsenic, sulfur) or crystals such as sapphire or yttrium aluminum garnet, which are highly-transparent in the appropriate spectral range, or other host crystals of the respective laser media or, for example, silicon, germanium or zinc selenide.

The invention is not limited in its embodiment to the above-disclosed, preferred embodiment. Rather, a number of variations are conceivable which use the illustrated solution, even in fundamentally differently configured embodiments.

We claim:

1. An improved Q-switched laser system for emitting laser pulses having a laser pulse length, the Q-switched laser system including means for providing a resonator, a laser-active medium in the resonator, an optical pumping means, and a passive Q-switch, wherein the improvement comprises:

the means for providing a resonator comprises resonator extension means for increasing the laser pulse length, the resonator extension means including an optical waveguide.

2. A Q-switched laser system according to claim 1, wherein the optical pumping means comprises means for stimulating the laser-active medium with a pumping energy which is higher than the pumping energy required for generating single pulses, so as to produce a cascade of pulses in a burst.

3. A Q-switched laser system according to claim 2, wherein the optical pumping means comprises means for emitting energy which is higher by 30% or more than the necessary pumping energy.

4. A Q-switched laser system according to claim 2, further comprising means for displaying the occurrence of the pulse cascade.

5. A Q-switched laser system according to claim 2, wherein the optical waveguide includes an optical fiber comprising material selected from the group consisting of quartz glass, chalkogenide glass, and zirconium fluoride.

6. A Q-switched laser system according to claim 5, wherein the optical fiber has a numerical aperture of about 0.2.

7. A Q-switched laser system according to claim 2, wherein the optical waveguide includes an optical fiber which follows a coiled or membering path in order to attain a large effective optical length in structure with a small length.

8. A Q-switched laser system according to claim 2, wherein the optical waveguide comprises a planar multi-pass waveguide.

9. A Q-switched laser system according to claim 2, wherein the means for providing a resonator includes a partially transparent concave mirror, and further comprising a collimation lens between the laser-active medium and the partially-transparent concave mirror, and wherein the passive Q-switch is disposed between the collimation lens and the partially-transparent concave mirror.

10. A Q-switched laser system according to claim 9, further comprising means for frequency doubling, the means for frequency doubling being disposed between the collimation lens and the partially-transparent concave mirror.

11. A Q-switched laser system according to claim 1, wherein the resonator extension means has an effective optical length which is predetermined such that each laser pulse has a temporally and spatially smoothed pulse profile.

12. A Q-switched laser system according to claim 1, wherein the resonator extension means has an effective optical length which is selected to attain a pulse length in a range between 0.2 and a few $\mu s$.

13. A Q-switched laser system according to claim 1, wherein the laser-active medium comprises a laser crystal which is selected from the group consisting of Nd:YAG, alexandrite of titanium sapphire, and a crystal having Er doping.

14. A Q-switched laser system according to claim 1, wherein the laser-active medium comprises a laser crystal which possesses double-refracting properties, and which is selected from the group consisting of $Nd:YAlO_3$ and Nd:YLF.

15. A Q-switched laser system according to claim 1, wherein the laser-active medium is gaseous, and particularly includes an inert-gas halogenide (excimer or exciplex).

16. A Q-switched laser system according to claim 1, wherein the optical waveguide includes an optical fiber having transmission properties which are matched to the laser-active medium, the optical fiber comprising material selected from the group consisting of quartz glass, chalkogenide glass, and zirconium fluoride.

17. A Q-switched laser system according to claim 16, wherein the optical fiber has a numerical aperture of about 0.2.

18. A Q-switched laser system according to claim 16, wherein the optical fiber has an end, and wherein the optical waveguide further includes a spliced-on taper at the end of the optical fiber.

19. A Q-switched laser system according to claim 1, wherein the optical waveguide includes an optical fiber having a coiled or meandering arrangement in order to attain a large effective optical length in a structure with a small length.

20. A Q-switched laser system according to claim 1, wherein the optical waveguide comprises a planar multi-pass waveguide.

21. A Q-switched laser system according to claim 1, wherein the resonator extension means includes a low-aberration collimation lens, wherein the means for providing a resonator includes a concave retroreflector, and wherein the optical waveguide includes a fiber coil communicating between the lens and the retroreflector.

22. A Q-switched laser system according to claim 1, wherein the means for providing a resonator includes a partially-transparent concave mirror, and further comprising a collimation lens between the laser-active medium and the partially-transparent concave mirror, and wherein the passive Q-switch is disposed between the collimation lens and the partially-transparent concave mirror.

23. A Q-switched laser system according to claim 22, further comprising a means for frequency doubling, the means for frequency doubling including a doubling crystal which is disposed in which is between the collimation lens and the partially-transparent concave mirror.

24. A Q-switched laser system according to claim 1, further comprising means, including a polarization beam splitter, for generating polarized radiation.

25. A Q-switched laser system according to claim 1, wherein the system is constructed from three pre-adjusted assemblies.

26. A Q-switched laser system according to claim 1, wherein the resonator extension means increases the laser pulse length so as to attain a laser pulse length that is greater than about 200 ns.

27. A Q-switched laser-system which emits laser pulses having a laser pulse length, comprising:

first and second mirrors, one of the first and second mirrors being partially transparent;

a laser-active medium which is disposed in an optical path extending between the mirrors;

an optical pump to supply energy to the laser-active medium;

a Q-switch in the optical path; and an optical waveguide in the optical path to lengthen the optical path by at least a plurality of meters, wherein the lengthening of the optical path by the optical waveguide is selected so a to attain a laser pulse length that is greater than about 200 ns.

28. A Q-switched laser system according to claim 27, wherein the optical waveguide comprises optical fiber.

29. A Q-switched laser system according to claim 27, wherein the optical waveguide comprises as a planar, multi-pass waveguide.

30. A Q-switched laser system according to claim 27, wherein the optical waveguide lengthens the optical path by about 18 meters.

* * * * *